(12) United States Patent
Haag et al.

(10) Patent No.: US 10,662,151 B1
(45) Date of Patent: May 26, 2020

(54) PROCESS FOR PREPARING DTEA HCL

(71) Applicant: AMSA, Inc., Auburn, MI (US)

(72) Inventors: Anthony P Haag, Bozeman, MT (US); Pulikkottil Jacob Thomas, Midland, MI (US)

(73) Assignee: AMSA, Inc., Auburn, MI (US)

( * ) Notice: Subject to any disclaimer, the term of this patent is extended or adjusted under 35 U.S.C. 154(b) by 0 days.

(21) Appl. No.: 16/233,765

(22) Filed: Dec. 27, 2018

Related U.S. Application Data

(60) Provisional application No. 62/612,367, filed on Dec. 30, 2017.

(51) Int. Cl.
| | | |
|---|---|---|
| *C07C 319/26* | (2006.01) | |
| *C07C 323/25* | (2006.01) | |
| *C07C 319/18* | (2006.01) | |
| *A01N 33/08* | (2006.01) | |
| *A01N 25/22* | (2006.01) | |

(52) U.S. Cl.
CPC .......... *C07C 319/26* (2013.01); *C07C 319/18* (2013.01); *C07C 323/25* (2013.01); *A01N 25/22* (2013.01); *A01N 33/08* (2013.01)

(58) Field of Classification Search
None
See application file for complete search history.

(56) References Cited

U.S. PATENT DOCUMENTS

| | | |
|---|---|---|
| 5,025,038 A | 6/1991 | Relenyi |
| 5,087,757 A | 2/1992 | Mariam et al. |
| 5,206,225 A | 4/1993 | Horstmann et al. |
| 5,369,118 A | 11/1994 | Reizlein et al. |
| 5,371,105 A | 12/1994 | Damo et al. |
| 7,368,466 B2 | 5/2008 | Beilfuss et al. |
| 2008/0076803 A1 | 3/2008 | Beilfuss et al. |
| 2013/0217579 A1 | 8/2013 | Wacker et al. |

FOREIGN PATENT DOCUMENTS

WO    WO2001/041570 A2    6/2001

OTHER PUBLICATIONS

Matsugi ("2,2'-Azobis(2-methylpropanimidamide) dihydrochloride (V-50)" e-ROS Encyclopedia of Reagents for Organic Synthesis, 2007, p. 1-2) (Year: 2007).*
Havel, James J. and Brady, Bonnie M. F., US H1265, Statutory Invention Registration, published Dec. 7, 1993.

* cited by examiner

*Primary Examiner* — Amy C Bonaparte
(74) *Attorney, Agent, or Firm* — Technology Law PLLC; Karen L. Kimble

(57) ABSTRACT

The present invention provides an improved process for preparing DTEA HCl from decene and cysteamine HCl by using a catalyst, solvent and a co-solvent to aid the reaction and provide low temperature stabilization of the resulting product solution.

15 Claims, 2 Drawing Sheets

Solubility of Crude DTEA HCl in Water.

PROCESS FOR PREPARING DTEA HCL

BACKGROUND OF THE INVENTION

Field of the Invention

This invention generally concerns an improved process for preparing DTEA HCl from 1-decene and cysteamine HCl (CA HCl).

Background of the Invention

Industrial chemicals are most commonly manufactured using solvent-based reaction methodology, followed by isolation, purification, and packaging. Many such chemical products are then formulated into a commercial product by blending the active ingredient (AI; see Glossary below for a full listing of abbreviations and acronyms) with other materials optimized for, and specific to, its end use. When formulated as an aqueous solution, often problems with freezing and or AI precipitation can become an issue when formulations are stored at (or in some cases, even briefly subjected to) below room temperature environments. Partial precipitation and settling of solids results in variable AI concentration as well as inaccurate and inefficient transfers of the formulation from storage to end-use vessels. Solids may cause major difficulties with clogging filters and/or nozzles in applications requiring the formulation be sprayed. Thus, solid or solid-liquid mixtures may require costly and inconvenient heating and agitation operations in order to regain homogeneity.

DESCRIPTION OF RELATED ART

Several patents disclosed use of additives in microbiocidal formulations to increase low temperature stability (to hinder AI precipitation or formulation solidification). A few of such patents are provided below. None of this next listed art uses LTS agents as a co-solvent for the reaction to make DTEA HCl.

US Pub Appln 2008/0076803 (Beilfuss) describes addition of one or more aromatic alcohols to 1,2-benzoisothiazolin-3-one formulations to increase low temperature stability. Specifically, the preferred additives are chosen from (i) aryloxyalkanols (glycol monoaryl ethers), (ii) arylalkanols and (iii) oligoalkanol aryl ethers or mixtures thereof. This work proscribes in Claim 13 a sequence for preparation of a formulation specifying the LTS is the last component to be added, and is not taught or used in any LTS-co-solvent process.

WO2001/041570 (Beilfuss) describes use of the same suite of additives as those in US 2008/0076803 above but they are used to improve the stability and lessen inhomogeneity of a different mixture of AIs.

US Pub Appln 2013/0217579 (Wacker) describes a new low temperature solvent for pesticide formulations and includes addition of LTSs propylene glycol (PG) and glycerol to said formulations.

U.S. Pat. No. 5,371,105 (Damo) describes novel aqueous formulations of agrochemical active substances which are sparingly soluble in water. These formulations are either water-in-oil or oil-in-water emulsions. One additive to the formulation is an LTS, preferably glycerol, but also mentions EG, PG, and polyglycols.

U.S. Pat. No. 5,369,118 (Reizlein) teaches the use of LTS auxiliaries to improve the stability of triazole fungicide formulations to retard solids formation in aqueous spray liquors to prevent clogging spray nozzles and in-line filters. PG and glycerol are preferred.

U.S. Pat. No. 5,206,225 (Horstmann) teaches use of LTS auxiliaries to improve the stability of triazole fungicide formulations to retard solids formation in aqueous spray liquors to prevent clogging spray nozzles and in-line filters. PG and glycerol are preferred.

U.S. Pat. No. 7,368,466 (Beilfuss) discloses a water-based formulation of the fungicide, a salt of carbedazim, containing certain LTSs exhibit long-lasting low temperature stability. Beilfuss, et al. cite benzyl alcohol (BA) as a preferred LTS and 1-phenoxy-2-propanol (PP) as a particularly preferred LTS; neither of these is a satisfactory LTS-co-solvent in the DTEA HCl process described herein.

U.S. Pat. No. 5,087,757 (Mariam/Sinclair) taught the use of various solvents in the reaction of 1-decene and CA HCl (2-aminoethanethiol hydrochloride, also referred to as cysteamine HCl) to produce DTEA HCl using catalysts/initiators including hydrogen peroxide and azo initiators. These included glycols and glycol ethers, and their mixtures with water. Examples mentioned are: ethylene glycol; propylene glycol; propylene glycol methyl ether; dipropylene glycol methyl ether; diethylene glycol; triethylene glycol; tetraethylene glycol; and dipropylene glycol, with propylene glycol and tetraethylene glycol preferred. Some of the disadvantages of using the Mariam/Sinclair reaction to produce DTEA HCl are: (1) achieving high conversion of reactants is difficult and requires multiple additions of catalyst and extended reaction times to achieve high conversion of reactants to DTEA HCl; and (2) dilution with the preferred solvent (water) produces a formulation with serious solids formation problems at low temperatures (defined as about 32° F. to about 60° F.). The Mariam/Sinclair reaction to produce DTEA HCl US H1265 Statutory Invention Registration (Havel) taught a variety of alcohol (hydroxyl group-containing) additives that could be added to the DTEA HCl reaction product prepared by the Mariam process (using PG or tetraethylene glycol (TEG) as a reaction solvent). This Havel technique dilutes the reaction product mixture with an LTS to provide low temperature stability. LTS solvents mentioned are butyl alcohol, cyclohexanol, hexyl alcohol, isobutyl alcohol, ethylene glycol phenyl ether (a synonym for 2-phenoxyethanol (PE)) and propylene glycol phenyl ether (a synonym for 1-phenoxy-2-propanol (PP)) and mixtures thereof. Some of the disadvantages of using Havel's LTS with the products of these processes are: 1) addition of the LTS to the organic solvent-based reaction mixture results in higher overall product costs; and 2) adding additional organic chemicals to the formulation is problematic in the application of this product in industrial water treatment: organic solvents in the formulation are nutrients for microbial growth and make its control more challenging and costly. The amount of organic solvent in the formulation should be minimized to the extent possible.

U.S. Pat. No. 5,025,038 (Relenyi) describes an ETOX process using PG as solvent to make DTEA HCl to afford low temperature stability; however, this process has similar solids formation problems as Havel at low temperatures.

Clearly, there is still a need for a better process to make DTEA HCl in order to: obtain effective contact of the reactants in the reaction process to obtain high reactant conversion and yield; have a final homogeneous liquid product formed after the process with no solids formation occurring at lower temperatures such as 32° F.; control microbial growth by limiting adding more organic components; have a more economical process by using a solvent serving as both a reaction co-solvent and LTS that eliminates a further step for the addition of LTS; and have ease of handling with low environmental impact by using a larger portion of an aqueous based system for the reaction.

BRIEF SUMMARY OF THE INVENTION

The present invention describes an improvement over known processes for the production of n-decylthioethylamine HCl (DTEA HCl) in which the reaction efficiency is improved and incorporates an Additive that is both a low temperature stabilizer (LTS) and a reaction Co-solvent to provide a commercial formulation with improved low temperature stability with minimal post reaction processing. Use of the claimed Additive in the reaction, as well as the final formulation, eliminates the need of a separate reaction solvent and thereby reduces the production cost.

More specifically, the present invention concerns a process for preparing n-decylthioethylamine HCl (DTEA HCl) comprising reacting decene and cysteamine HCl, with (a) a catalyst, (b) water, and (c) an Additive of the formula:

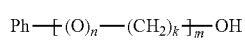

Formula (A)

wherein:
Ph is phenyl;
n is 0 or 1;
k is 2-4; and
m is 1-3;
that provides the n-decylthioethylamine HCl, in about >90% yield, as a low temperature, stable liquid product after dilution with water.

Additional Additive can be added after the reaction is completed or as part of the dilution. The amount of Additive present in the final solution is from about 1 to about 30 wt % or from about 2 to about 20 wt %.

The low temperature stability of the resulting product means at temperatures from about 32° F. to about 60° F. A stable liquid product means that the product has no solids formation or separation of any phases at the low temperatures.

The amount of product present in the final solution is from about 2 to about 25 wt %; or from about 5 to 15 wt %.

The yield of the DTEA HCl product from the present reaction is >90%, often >95%, even when run on a commercial scale and can be further optimized.

The selection of the Additive and catalyst used in this process is not trivial and discussed further below.

DETAILED DESCRIPTION OF THE INVENTION

Figure 1:
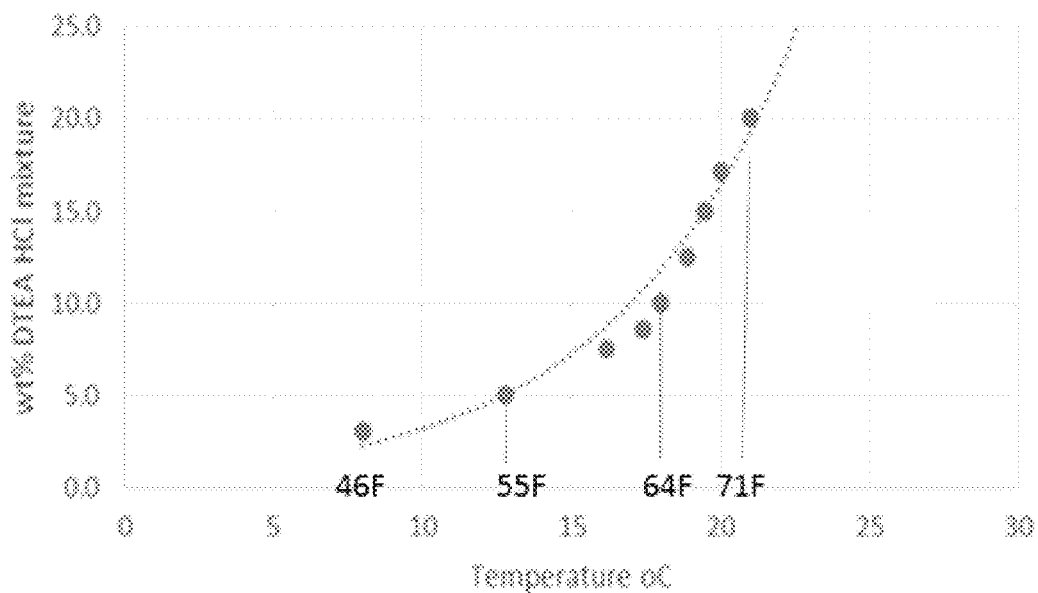
FIG. 1 graphically represents the water solubility of crude DTEA HCl (approximately 50% DTEA HCl, 20% PG, 30% water). There is no LTS used so the data is comparative.

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

The following terms as used in this application are to be defined as stated below and for these terms, the singular includes the plural.

Additive means a compound that is both a Co-solvent (defined below) and an LTS (defined below)
AI means active ingredient
azo catalyst means, preferably, one of the following:
  2,2'-Azobis[N-(2-carboxyethyl)-2-methylpropionamidine];
  2,2'-Azobis[2-(2-imidazolin-2-yl)propane] dihydrochloride (VA 044);
  2,2'-Azobis[2-methyl-N-(2-hydroxyethyl)propionamide];
  4,4'-Azobis(4-cyanovaleric acid); or
  2,2'-Azobis(2-methylpropionamidine) dihydrochloride (V-50)
BA means benzyl alcohol, as depicted by the following structure

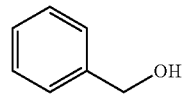

CA means cysteamine or 2-aminoethanethiol or 2-mecaptoethylamine
Co-solvent means the solvent used with water in the reaction
Decene means 1-decene, $C_{10}H_{20}$
DiEPh means diethyleneglycol phenylether or 2-(2-phenoxyethoxy)ethanol, as depicted by the following structure

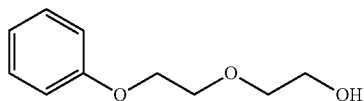 [SMILES: OCCOCCOc1ccccc1]

DTEA means n-decylthioethylamine or 1-decylthioethylamine or 2-(1-decylthio)ethylamine
g means grams
h means hour or hours
HCl means a hydrochloride salt
L means liter LTS means low temperature stabilizer, where low temperature is defined as from about 32° F. to about 60° F.

min means minute or minutes mL means milliliter

PA means 2-phenylethanol as depicted by the following structure

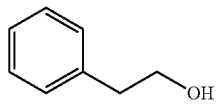

PE means 2-phenoxyethanol, as depicted by the following structure

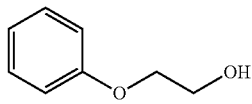

PG means propylene glycol, as depicted by the following structure

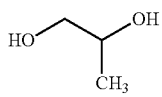

PP means 1-phenoxy-2-propanol, as depicted by the following structure

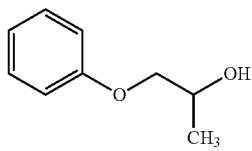

RT means room temperature or ambient temperature, from about 20° C. to about 25° C. or about 72° F.

sec means second

Solids formation includes but is not limited to formation of a solid phase within the original liquid phase, which includes but is not limited to crystallization; if the amount of solid is substantial, the entire volume may appear solid Water means water purified by reverse osmosis (RO) as used in the present examples, but this is not critical wt % means percent by weight Discussion In aggregate, the above prior art establishes the utility of low-temperature stabilizers in formulations but provides no guidance for selection of an LTS that would be a suitable co-solvent for a DTEA HCl manufacturing process. The philosophy that emerges in these prior teachings is that low temperature stabilizers are thought of as an interchangeable, generic class such that one may simply choose any one of a myriad of known LTS agents. These LTS agents are generally the last component of the formulation to be described and commonly include the phrase 'as needed'. There is no overlap in the LTS s taught by Havel and the co-solvents taught by Mariam. Indeed, we have found that most LTSs are not generally good reaction co-solvents and also that good co-solvents are not generally good as a LTS.

Present Process

An improved process is needed to avoid the increased processing time and costs, to improve the conversion of reactants, and to improve the yield DTEA HCl. It would also be advantageous to use only water for dilution of the DTEA HCl reaction mixture to provide a commercial formulation. Replacing currently used DTEA HCl reaction co-solvents with a low temperature stabilizer as a co-solvent avoids the solids formation issue of such formulations. Using traditional non-LTS co-solvents, then adding an LTS in the post production formulation process, requires additional equipment and complicates formulation. The presence of non-LTS co-solvent in the commercial formulation (as done in the prior art processes) dilutes the AI, adds unnecessary cost to production, and essentially serves only as food for microorganisms in a water treatment environment. Another factor when considering an organic material for use as a co-solvent concerns flammability. Solvents with higher flash points are preferred over low flash point solvents whenever possible. For example, considering two of Havel's mentioned LTS, namely PE and 1-butanol, if both actually worked as a co-solvent in the DTEA HCl process, PE (flash point 250° F.) would be the preferred solvent over 1-butanol (flash point 96° F.) on this basis.

A preferred form of DTEA HCl for sale is a liquid in various concentrations, for example about 5 to about 15 wt % DTEA HCl, whereas the DTEA HCl is produced most efficiently at a higher concentration in the reaction. Thus the reaction mixture must be diluted to yield the final formulation for sale. Water is the preferred dilution solvent due to its low toxicity and low cost and environmental preference. Also water is not a nutrient for microbial growth during product application, so lowering organic solvent content by increasing the water content provides benefit in applications. Unfortunately, even at these low concentrations of DTEA HCl, aqueous mixtures prepared by dilution of the reaction product produced by the Mariam process (above) begin to solidify at temperatures that are commonly used in storage and handling (32° F. to 60° F.). Concentrations as low as 1-5 wt % showed problematic solids formation. It should also be noted that dilution of the crude product with additional propylene glycol, both a preferred reaction co-solvent taught by Mariam and a commonly used LTS in many applications, is NOT effective for this present process. That is, PG is not an effective LTS in this application. It would be of great value to be able to use a different co-solvent that BOTH afforded a high reaction yield of DTEA HCl and functioned as an effective low temperature stabilizer (LTS) in the diluted, end-use product.

The reactants for this present process are decene (which is soluble in several organic solvents and relatively insoluble in water), and CA HCl (which is soluble in aqueous systems). The present process requires a water solvent with an organic co-solvent that serves multiple functions (including improving homogeneity of the reaction process and also providing an LTS for the product formulation), and a catalyst. When these two reactants are mixed with the solvents and catalyst, the reaction occurs. An Additive is needed as a Co-solvent to ensure effective contact and reaction of the reactants in the initial two phase mixture in a high reaction yield, which also serves as an LTS for the final product that is needed for handling and storage. Finding an Additive that will work as both a Co-solvent and a LTS in this specific reaction has not proven easily done. The formulation of DTEA HCl (product) from the reaction must remain as a homogenous liquid to provide accurate and simple transfer of the product without phase separation such as solids formation by crystallization (which is a problem in prior systems). Aqueous solutions with minimal organic content are preferred in this process and its ultimate formulation as they are inexpensive, relatively non-hazardous, and especially, provide minimal organic nutrients for microbial growth in end use applications.

Water and a LTS Used as a Co-Solvent

Prior teachings suggest that aqueous propylene glycol (PG) is the reaction solvent of choice. However, the product obtained from a PG-based process when diluted with water unfortunately forms solids at low temperatures (as defined above) and requires addition of a LTS to achieve a homogeneous liquid at these low temperatures.

Havel taught the use of LTS such as 2-phenoxyethanol (PE) and 1-phenoxy-2-propanol (PP) with the DTEA HCl product to provide stable, homogeneous liquids at low temperature. These LTS were not used in the reaction but added after the product was formed. None of the LTS agents that were found successful by Havel were used or taught as a co-solvent for the reaction. It would be more cost effective and efficient when the LTS is also used as a co-solvent in the reaction as it eliminates the need for and cost of any other co-solvent used strictly for the reaction step, such as propylene glycol (PG). Thus in a streamlined process the formulated product can maintain its low temperature stability without the usual operation steps of separating the co-solvent from the reaction mixture to isolate the AI to which the LTS is added in a separate formulation step.

The present process uses an Additive that is both a Co-solvent and an LTS. This has the advantages given below. Determining what Co-solvent that works well for the present reaction and is also a LTS was neither appreciated nor attempted by the prior art.

However, choice of an LTS that is also a good reaction Co-solvent is not a trivial exercise. A commonly used and widely preferred LTS such as propylene glycol (PP), glycerol and ethylene glycol are not good as LTS for DTEA HCl. These prior art LTS do not function well or at all in the present process. Neither is an aromatic ring functional group a sufficient criterion for selection of an LTS as a co-solvent, e.g., neither benzyl alcohol (BA) nor 1-phenoxy-2-propanol (PP) is an effective co-solvent for the present DTEA HCl reaction using $H_2O_2$ or azo catalysts in the present invention, although both are known as excellent LTS.

The present Additives that are Co-solvents used in the present reaction and used as LTS, can be optionally further added to the aqueous DTEA HCl product solution to provide a stable liquid at temperatures down to at least 32° F.

A formulation that forms solids at low temperatures such as these which are commonly encountered in storage and use of this product is not practical and is problematic. When solids form in a formulation, it is often difficult to regain homogeneity. Storage in specially heated storage areas to prevent lower temperatures or using heat and agitation to melt and re-blend the mixture is time-consuming, expensive and inconvenient. Heterogeneous mixtures are difficult to pump, can clog nozzles and filters, do not meter well, and cannot be used to provide consistent or accurate dosing.

Suitable Co-solvents of the present invention are phenyl containing alcohols, such as 2-phenoxyethanol (PE) and 2-phenylethanol (PA), preferably those having a significant water solubility of about 1 to about 10 wt %. The amount of Additive (low temperature stabilizer/Co-solvent) used in the reaction is from about 10 to about 49 wt %, and preferably from about 15 to about 35 wt %. The effective Additives are represented by the following Formula A:

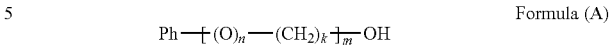

Formula (A)

wherein:
Ph is phenyl;
n is 0 or 1;
k is 2-4; and
m is 1-3.

Representative examples of such Additives of Formula A are PA, PE, and DiEPh. Some examples of LTSs found ineffective as Co-solvents are BA, PP and PG. Thus it is not apparent to one skilled in this art what will work as an Additive in the process based on prior known reactions.

When carrying out the current reaction, the mixture initially has two liquid phases; namely, an organic phase containing decene and an aqueous phase containing cysteamine HCl (CA HCl). The latter aqueous phase also contains the catalyst. While not wishing to be bound by theory, it is believed that for reaction to occur efficiently, decene must have sufficient solubility in or contact with the aqueous phase. The present phenyl alcohol Co-solvents have a suitable balance of polar and nonpolar character which facilitates the required mixing and solubilization in the reaction. These Co-solvents also possess suitable properties to solubilize the final product at low temperatures from about 32° F. to about 60° F. to avoid solids formation and/or or phase separation as LTS agents. These present LTS are present in the final product solution from about 1 to about 30 wt %, preferably from about 2 to about 20 wt %. Many of the prior used solvents do not have such properties and do not provide these desired results.

Catalyst/Initiator

The present process requires that a free radical initiator is used. When the Co-solvent is used with various catalysts/initiators there is the issue of solubility and which ones will work in the system. For example, hydrogen peroxide and the azo initiator (including non-water soluble azo initiators) are taught by Mariam (discussed above). However the preferred azo initiators that taught were azobisnitriles which are not water soluble. Mariam also provided no data for the azo initiators, which have been found in this present testing that even water soluble azo initiators are not effective with PG as the solvent. However, surprisingly, an azo catalyst with PE or PA solvent in the present reaction alone resulted in the desired LTS product.

The present preferred catalysts are azo catalysts that are water soluble such as:
2,2'-Azobis(2-methylpropionamidine) dihydrochloride (V-50);
2,2'-Azobis[N-(2-carboxyethyl)-2-methylpropionamidine];
2,2'-Azobis[2-(2-imidazolin-2-yl)propane] dihydrochloride (VA-044);
2,2'-Azobis[2-methyl-N-(2-hydroxyethyl)propionamide]; and
4,4'-Azobis(4-cyanovaleric acid).

Selection of these various reaction parameters is not simple to obtain the desired results. Even though Havel's results showed 2-phenoxyethanol (PE) and PP to be good LTS for the diluted reaction product (added after the reaction was run), and Mariam teaches that good reaction solvents are specific glycols and glycol ethers, Mariam did not teach any of Havel's claimed LTS as reaction solvents and did not teach any phenyl-substituted alcohols of Formula (A). The present results show that good LTS are not necessarily good reaction solvents (e.g., BA and PP) and, vice versa, good reaction solvents are not good LTS [e.g., PG (present data and Havel), Dowanol DPM (dipropylene glycol methyl ether, Havel)]. Thus, it is not apparent to a skilled person how to identify a solvent that is successful for both purposes, i.e., an Additive. Indeed it was surprising that two structurally similar compounds taught by Havel as a good LTS (2-phenoxyethanol (PE) and PP) gave greatly different results as reaction solvent, good and poor, respectively. Another solvent which now is identified as an excellent LTS was BA; however, it proved to be a poor reaction solvent. Another good Co-solvent diethylene glycol phenyl ether (Dowanol DiEPh) has been found to also be a good LTS for DTEA HCl. The present data and observations indicate that successful reaction results not only depend on the solvent but also the catalyst. Comparison of data in Tables 1 and 2 show good results with $H_2O_2$ but poor results with V-50.

If a skilled person was to randomly screen a list of solvents taught by Havel and other solvents of similar structure (such as alcohols) with both $H_2O_2$ and V-50 (and possibly other commercially available free radical initiators), as well as at varying solvent concentrations and with varying amounts of water, the number of combinations to test would be very large and require undo experimentation and an impractical amount of time to test, making the ultimate selection of successful reaction solvent for this present process not practical. A method to just find them by testing is daunting as the list to test would be very large with multiple conditions and the reaction actually run to determine what was effective for the desired results. Thus this is not a simple substitution of a few items to see what would work; rather it requires multiple variables and undue experimentation to find what is now claimed.

Clearly, previous attempts to make DTEA HCl have had difficulties obtaining high reactant conversion and yields, to have no phase separation or solids formation at lower temperatures such as 32° F. without an LTS; to control microbial growth by limiting organic components; to not require separation steps of the solvent or product; and to have ease of handling with low environmental impact by using a larger portion of an aqueous based system. The present process provides these advantages.

This process provides a final product which is formed from the present reaction as a solution containing: a) from about 2 to 25 wt % of DTEA HCl, preferably from about 5 to about 15 wt %, b) additional water and Additive added after the reaction if needed in an amount from about 1 to about 30 wt % of Additive, preferably from about 2 to about 20 wt %. The final product provides a low temperature stability of at least from 32° F. to about 60° F. The invention will be further clarified by a consideration of the following examples, which are intended to be purely exemplary of the invention.

The letter examples are comparative examples. The numbered examples are directed to the compounds of the present invention.

Materials

Decene was purchased from Shell.
DiEPh was obtained from DowDupont.
PE was obtained from Nexeo.
Benzyl alcohol and PA were purchased from Sigma-Aldrich.
PP was obtained from GNS Technologies LLC.
CA HCl was purchased from Hangzhou Qianjin Technology Ltd.

Water is prepared by reverse osmosis (RO).
V-50 was purchased from Wako.
VA-044 was obtained from Sigma-Aldrich.
$H_2O_2$ was purchased from GFS Chemicals, Inc., as a 50% aqueous solution and then diluted to 1.5-1.8% solution with water.
DTEA HCl was made by the method described in U.S. Pat. No. 5,087,757 and isolated by dilution and crystallization with acetonitrile.

General Reaction Conditions

The general present reaction conditions are:
Temperatures from about 25° C. to about 120° C. (preferably from about 74° C. to 77° C. preferred);
Atmosphere is air, nitrogen or argon;
Catalyst concentration from about 0.01 to about 5 wt %, preferably from about 0.1 to about 1 wt %;
Decene concentration from about 1 to about 40 wt %, preferably from about 15 to about 30 wt %;
Cysteamine HCl concentration from about 1 to about 40 wt %, preferably from about 15 to about 30 wt %;
Water concentration from about 10 to about 49 wt %, preferably from about 15 to about 35 wt %;
Additive concentration from about 10 to about 49 wt %, preferably from about 15 to about 35 wt %; and
Optionally are: 36 wt % HCl added from about 0.01 to about 1 wt %; DTEA HCl added from about 1 to about 5 wt %, preferably from about 0.5 to about 2 wt %.

Preparation of DTEA HCl and Comparatives

Example 1: General Procedure for $H_2O_2$ as the Catalyst

Using 72 g of decene, 62 g of CA HCl, 50-75 g of Co-solvent, 44 g of water, 2.75 g of DTEA HCl, 26-30 mL of $H_2O_2$, 0.1 mL of concentrated HCl, the following general process was run with the various Co-solvents indicated.

To a three necked flask equipped with mechanical stirrer, thermocouple, addition funnel and nitrogen inlet, cysteamine HCl, Co-solvent, water and DTEA HCl were added. The system was flushed with nitrogen and the reaction was carried out under the atmosphere of nitrogen. The mixture was stirred and heated to 65° C. using a water bath. To this mixture 0.1 mL of concentrated HCl was added followed by 10 mL of decene. The addition of hydrogen peroxide solution was then started along with the remaining decene, maintaining the reaction temperature below 80° C. (about 74° C. to 77° C. is preferred). Hydrogen peroxide solution was added over a period of 40 min. and decene was added over a period of 20 min. The reaction mixture was stirred for another h after completion of the addition of hydrogen peroxide while maintaining the reaction temperature below about 80° C. (about 74° C. to about 77° C. temperature is preferred). The mixture was cooled and analyzed. The results are shown in the following Table 1.

TABLE 1

DTEA HCl Process Using Hydrogen Peroxide and Various Co-solvents

| Example | Co-solvent (g) | Aqueous $H_2O$ | DTEA HCl Yield % | Un-reacted decene % | Unreacted cys-teamine HCl % | Comments |
|---|---|---|---|---|---|---|
| 1 | Propylene glycol | 30 mL (1.5% | 84.4 | 4 | 3.5 | Reaction worker |

TABLE 1-continued

DTEA HCl Process Using Hydrogen Peroxide and Various Co-solvents

| Example | Co-solvent (g) | Aqueous H₂O | DTEA HCl Yield % | Un-reacted decene % | Unreacted cys-teamine HCl % | Comments |
|---|---|---|---|---|---|---|
| | (PG) (50.5 g) | solution) | | | | well in PG |
| 2 | 2-Phen-oxy-ethanol (PE) (75 g) | 27 mL (1.85% solution) | 83 | Not available | 3.9 | Reaction worker well in PE |
| A | Benzyl alcohol (BA) (50.5 g) | 27 mL (1.5% solution) | 10 | — | — | Not a good Co-solvent for the reaction. Three layers were formed |
| B | 1-Phen-oxy-2-propanol (PP) (75 g) | 30 mL (3.1% solution) | Not analyzed | 17.8 | Not analyzed | Not a good Co-solvent for the reaction. Two layers were formed |
| 3 | 2-Phenyl-ethanol (PA) (75 g) | 30 mL (3.1% solution) | Not analyzed | 1.63 | Not analyzed | Reaction worked well in PA |

The presence of two or three layers is evidence of low conversion and yield. These results show that PG, PE and PA are effective Co-solvents with $H_2O_2$ catalyst. BA and PP were not effective and only produced a low product yield.

Example 2: General Procedure for V-50 as the Catalyst

Using 72 g of decene, 62 g of CA HCl, 75 g of Co-solvent, 75 g of water, 2.75 g of DTEA HCl, 0.39-0.78 g of V-50 [2,2'-Azobis(2-methylpropionamidine) dihydrochloride] in 10 mL of RO water, 0.1 mL of concentrated HCl, the following general process was run with the various Co-solvents indicated.

To a three necked flask equipped with mechanical stirrer, thermocouple, addition funnel and nitrogen inlet, cysteamine HCl, co-solvent, water and DTEA HCl were added. The system was flushed with nitrogen and the reaction was carried out under an atmosphere of nitrogen. The mixture was stirred and heated using a water bath to 65° C. To this mixture 0.1 mL of concentrated HCl was added, followed by 10-15 mL of decene. About 5 mL of V-50 solution was then added and continued the stirring. The remaining decene was added dropwise to the reaction mixture over a period of 30-35 min. maintaining the reaction temperature below 80° C. (74° C. to 77° C. is preferred). Another portion of V-50 (5 mL) was added after the addition of about 50 mL of decene, and continued the stirring. Stirring was continued for another 1.5-2 h after completion of the addition of decene while maintaining the reaction temperature below 80° C. (about 74° C. to 77° C. is preferred). The mixture was cooled and analyzed. The results are shown in the following Table 2.

TABLE 2

DTEA HCl Process Using V-50 and Various Co-solvents

| Example | Co-solvent (g) | V-50 (g) | DTEA HCl Yield % | Un-reacted decene % | Unreacted cys-teamine HCl % | Comments |
|---|---|---|---|---|---|---|
| C | Propylene glycol (PG) (75 g) | 0.78 g in 10 mL water | — | — | — | PG is not a good solvent with V-50 catalyst |
| 4 | 2-Phen-oxyethanol (75 g) (PE) | 0.39 g in 10 mL water | 95 | 1.5 | 1.4 | Good solvent. Reaction worked well. |
| D | Benzyl alcohol (BA) (75 g) | 0.5 g in 10 mL water | 10 | — | — | BA is not a good Co-solvent. Three layers were formed |
| E | 1-Phen-oxy-2-propanol (PP) (75 g) | 0.78 g in 10 mL water | NA | 24 | NA | PP is not a good Co-solvent. Two layers were formed |
| 5 | 2-Phenyl-ethanol (PA) (75 g) | 0.78 g in 10 mL water | NA | 3.01 | NA | PA worked a good as PE based on decene consumption. |

NA = Not Analyzed

These results show that PE and PA were effective as Co-solvents. PG, PP and BA were not effective.

Example 3: Comparison of PE and PG

Addition of PE in the range of about 5 wt % to about 10 wt % to a 15 wt % DTEA solution (prepared from commercial DTEA HCl concentrate by diluting with water) produces homogeneous solutions at both RT and upon prolonged storage—several days—at 32° F. The weight percent DTEA HCl in the solutions after addition of PE ranges from about 6.5 wt % to about 7 wt %.

Similarly, addition of PE in the range of about 13 wt % to about 16 wt % to a 15 wt % DTEA solution (prepared from commercial DTEA HCl concentrate by diluting with water) produces homogeneous solutions at both RT and upon prolonged storage—several days—at 32° F. Below approximately 13 wt % PE the solution is homogeneous at RT, but solid at 32° F. The weight percent DTEA HCl in the solutions after addition of PE ranges from about 12.5 wt % to about 13 wt %.

It should be noted that like the reaction to manufacture DTEA HCl, these formulations require a delicate balance between water and organic Additive in order to maintain homogeneity. Addition of too much or too little of either can affect the low temperature stability to solidification and can also affect homogeneity of the mixture at higher temperatures due to phase separation. These studies contain only results in which the solutions remain homogeneous throughout the temperature range studied. Only solutions at the lower end of Additive concentrations effective as LTS of a given solution were studied. The goal is to add approximately the smallest amount of organic LTS that is effective since this is both economically and microbially prudent.

In a direct comparison of the effectiveness of PE relative to PG, a 16.7 wt % DTEA solution (prepared as described above for 7.5 and 15 wt % solutions) was diluted with either PE or PG to provide solutions that contain 13.9 wt % of DTEA HCl and 16.6 wt % of either PG or PE.

Both solutions were homogeneous at RT. The DTEA HCl formulation containing PE remained homogenous at 32° F. while the DTEA HCl/PG formulation rapidly solidified and remained solid.

Figure 2:
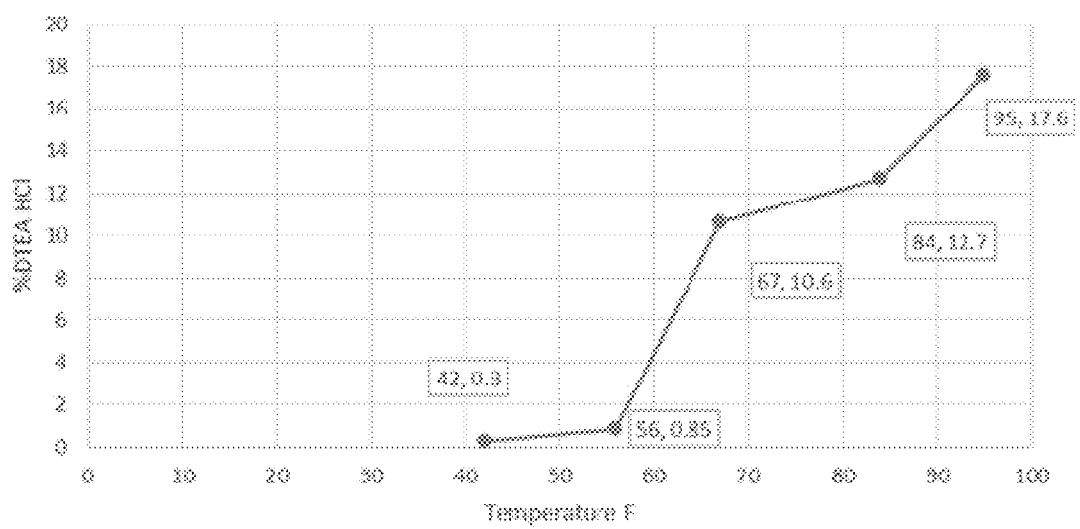
FIG. 2 graphically represents the water solubility of pure DTEA HCl. There is no LTS used so the data is comparative.

For further comparison, see FIG. 1, in which the solubility of crude DTEA HCl as a reaction product, produced using hydrogen peroxide catalyst and PG Co-solvent (containing approximately 50 wt % of DTEA HCl, 20 wt % of PG, and 30 wt % of water), was determined in water at different temperatures. Solids form in a 20% solution of the crude DTEA HCl reaction product at a temperature of 71° F. and after dilution with water to 5 wt % and the solution forms solids at 55° F. By comparison, the solubility of pure DTEA HCl in water is 11 wt % at 67° F. and less than 1 wt % at 56° F. (see FIG. 2).

Example 4: Procedure for 2,2'-Azobis[2-(2-imidazolin-2-yl)propane] dihydrochloride (VA 044) as the Catalyst The general procedure outlined in Example 2 was followed using 72 g of decene, 62 g of CA HCl, 75 g of co-solvent, 75 g of water, 2.75 g of DTEA HCl, 0.6 wt % of VA-044 in 10 mL of RO water. No solid DTEA HCL was added to this reaction. Analysis showed DTEA HCl was produced in 77.4% with 81% conversion in 2 h.

Example 5: Dilution Procedure

Part A: Propylene Glycol/Hydrogen Peroxide Process—Dilution with Water and 2-Phenoxyethanol (PE)

DTEA HCl product mixture (200 g, 50 wt % DTEA HCl) was mixed at RT with 380 g of water and 86.6 g of 2-phenoxyethanol (PE) to obtain 666.6 g of 15% DTEA HCl as a clear solution containing 13% of 2-phenoxyethanol (PE). Further 1:1 dilution at RT with water provided a 7.5% DTEA HCl as a clear solution containing 6.5% of 2-phenoxyethanol (PE).

Part B: 2-Phenoxyethanol/V-50 Process—Dilution with Water and 2-Phenoxyethanol (PE)

DTEA HCl product mixture (270 g, 47.4 wt % DTEA HCl) was mixed at RT with 544 g of water and 39 g of 2-phenoxyethanol (PE) to obtain 853 g of 15% DTEA HCl as a clear solution containing 13% 2-phenoxyethanol (PE) (270 g of the product mixture had already 72 g of PE). Further 1:1 dilution at RT with water provided a 7.5% DTEA HCl as a clear solution containing 6.5% of 2-phenoxyethanol (PE).

Example 6: Crystallization Behavior

Part A: Reaction Product from Propylene Glycol/Hydrogen Peroxide Process Diluted with Water and 2-phenoxyethanol (PE)

A 15% DTEA HCl solution containing 13% 2-phenoxyethanol and a 7.5% DTEA HCl containing 6.5% of 2-phenoxyethanol prepared from the crude product mixture obtained from propylene glycol/hydrogen peroxide process (Example 5A above) remained homogeneous liquids when the temperature was reduced to 32° F.

Also a 16.4% solution of DEA HCl containing 10.34% of PE upon storing in a refrigerator for two days did not result in any solids precipitation or crystallization.

As a comparison, this result with may be contrasted with FIG. 1 in which phenoxyethanol was not present and solids formation occurred at 32° F.

Part B: Reaction Product from 2-phenoxyethanol/V-50 Process Diluted with Water and 2-phenoxyethanol (PE)

1) A 15% DTEA HCl solution containing 13% 2-phenoxyethanol prepared from the crude product mixture obtained from 2-phenoxyethanol/V-50 process (Example 5B above) was a slightly cloudy solution at 32° F. However, no filterable solids were formed at this temperature.

As a comparison, this result with may be contrasted with FIG. 1 in which phenoxyethanol was not present and solids formation occurred at 32° F.

2) A 7.5% DTEA HCl solution containing 6.5% 2-phenoxyethanol prepared from the crude product mixture obtained from 2-phenoxyethanol/V-50 process (Example 5B above) was a homogeneous liquid at 32° F.

As a comparison, this result with may be contrasted with FIG. 1 in which phenoxyethanol was not present and solids formation occurred at 32° F.

Part C: Purified DTEA HCl Diluted with Water and 2-phenoxyethanol (PE)

A first 15% DTEA HCl solution containing 13% 2-phenoxyethanol and a second 7.5% of DTEA HCl containing 6.5% of 2-phenoxyethanol prepared from DTEA HCl (isolated by crystallization of the crude product mixture using acetonitrile) were both homogeneous liquids at 32° F.

In contrast, DTEA HCl is essentially insoluble in water at 32° F. and a 15 wt % DTEA HCl solution in water forms solids well above RT. (See FIG. 2).

Methods of Use of DTEA HCl

The product formed from the present process, DTEA HCl, is used in industrial water treatment systems for control of biofouling and corrosion.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A process for the preparation of 2-(n-decylthio)ethylamine HCl comprising reacting decene and cysteamine HCl with (a) a catalyst, (b) water, and (c) an Additive of the Formula (A):

Formula (A)

wherein:
Ph is phenyl;
n is 0 or 1;
k is 2-4; and
m is 1-3;
to provide the 2-(n-decylthio)ethylamine HCl as a concentrated reaction mixture in about >90% yield, wherein such concentrated reaction mixture is further diluted with water to provide a low temperature stable (LTS) liquid product.

2. The process of claim 1 wherein additional Additive is added directly to the concentrated reaction mixture, or as a part of the dilution with water, or after the dilution with water.

3. The process of claim 1 wherein the Additive is 2-phenoxyethanol (PE), 2-phenylethanol (PA) or diethyleneglycol phenylether (DiEPh).

4. The process of claim 1 wherein the catalyst is $H_2O_2$ or an azo catalyst.

5. The process of claim 4 wherein the azo catalyst is 2,2'-azobis[2-(2-imidazolin-2-yl)propane] dihydrochloride; 2,2'-azobis(2-methylpropionamidine) dihydrochloride; 2,2'-azobis[N-(2-carboxyethyl)-2-methylpropionamidine]; 2,2'-azobis[2-methyl-N-(2-hydroxyethyl)propionamide]; or 4,4'-azobis(4-cyanovaleric acid).

6. The process of claim 5 wherein the azo catalyst is 2,2'-azobis(2-methylpropionamidine) dihydrochloride.

7. The process of claim 1 wherein stable liquid product means without separation of a second phase or solids formation.

8. The process of claim 1 wherein the Additive is 2-phenoxyethanol (PE), 2-phenylethanol (PA) or diethyleneglycol phenylether (DiEPh) and the catalyst is 2,2'-azobis(2-methylpropionamidine) dihydrochloride.

9. The process of claim 1 wherein the Additive is 2-phenoxyethanol (PE), 2-phenylethanol (PA) or diethyleneglycol phenylether (DiEPh) and the catalyst is $H_2O_2$.

10. The process of claim 1 wherein 2-(n-decylthio)ethylamine HCl after the dilution with water is present from about 2 to about 25 wt %.

11. The process of claim 1 wherein 2-(n-decylthiol)ethylamine HCl after the dilution with water is present from about 5 to about 15 wt %.

12. The process of claim 1 wherein the amount of Additive present after the dilution with water is present from about 1 to about 30 wt %.

13. The process of claim 1 wherein the amount of Additive present after the dilution with water is present from about 2 to about 20 wt %.

14. The process of claim 1 wherein the amount of Additive used in the reaction is from about 10 to about 49 wt %.

15. The process of claim 1 wherein the reaction is run under an inert atmosphere, at a temperature from about 70° C. to about 79° C.

\* \* \* \* \*